(12) United States Patent
Matsumoto

(10) Patent No.: US 6,328,698 B1
(45) Date of Patent: Dec. 11, 2001

(54) DIAGNOSTIC SYSTEM AND METHOD FOR CORONARY ARTERY DISEASE AND OTHERS

(76) Inventor: Hiroshi Matsumoto, 14-17-204, Nishikata 1-chome, Bunkyo-ku, Tokyo (JP)

( * ) Notice: Subject to any disclaimer, the term of this patent is extended or adjusted under 35 U.S.C. 154(b) by 0 days.

(21) Appl. No.: 09/375,523

(22) Filed: Aug. 17, 1999

(30) Foreign Application Priority Data

Aug. 18, 1998 (JP) .................................................. 10-232017

(51) Int. Cl.[7] ........................................................ A61B 5/02
(52) U.S. Cl. ................................................................ 600/481
(58) Field of Search ..................................... 600/481, 504, 600/485, 488, 500, 534, 479, 300

(56) References Cited

U.S. PATENT DOCUMENTS 5,309,922 * 5/1994 Schechter et al. .................... 600/534
5,617,869 * 4/1997 Austin et al. ......................... 600/504

* cited by examiner

Primary Examiner—Eric F. Winakur
Assistant Examiner—Brian Szmal
(74) Attorney, Agent, or Firm—Armstrong, Westerman, Hattori, McLeland, Naughton, LLP

(57) ABSTRACT

The present invention aims at providing a diagnostic system for coronary artery disease and others and a diagnostic method using the above diagnostic system, which can detect vibration signal of murmur deriving from stenosis of coronary artery in its early stages, for it is possible to diagnose abnormal condition, prevent and treat heart disease. Disclosed is a diagnostic system for coronary artery disease comprising a detector of vibration signal of subject using pulsed laser beam, which is placed apart from the subject, and a detector of vibration signal of environmental noise, and vibration signal detected by the detector of vibration signal of subject and the detector of vibration signal of environmental noise is filtered for canceling internal noise and external noise, and the filtered vibration signal is amplified and recorded. The above detector of vibration signal of subject has one or a plurality of laser source head and vibration detective sensor with laser displacement gage and three-axial accelerometer, and the detector of vibration signal of environmental noise has three-axial accelerometer and supersensitive microphone.

9 Claims, 5 Drawing Sheets

DIAGNOSTIC SYSTEM AND METHOD FOR CORONARY ARTERY DISEASE AND OTHERS

BACKGROUND OF THE INVENTION a) Field of the Invention

The present invention relates to a (acoustically non-invasive) diagnostic system for coronary artery disease and others with a complex-multiple sensor system, which is usable in a bedside, and a diagnostic method for coronary artery desease and others using the above diagnostic system, more particularly, a diagnostic system for coronary artery disease and others having a set of detectors which detects very minute vascular murmur such as coronary artery stenotic, diastolic and other murmur, and a diagnostic method for coronary artery desease and others using the diagnostic system.

b) Description of Prior Arts

It is regulated in the Japanese Industrial Standard that a phonocardiograph can detect a heart sound signal of the frequency between 20 to 600 Hz, and the heart sound signal is that vibration signal deriving from heart and blood vessel is transmitted to body surface, which contains cardiac murmur.

The phonocardiograph comprises a heart sound microphone, a eqalizer (in the case of using a direct conductive microphone like an accelerometer microphone or a velocity microphone), a heart sound recorder, an electrocardiograph and a power supply, and it records the heart sound signal and the electrocardiographic signal simultaneously.

There are an aerial conductive microphone and the direct conductive microphone containing the accelerometer microphone or the velocity microphone and others as the heart sound microphone, and the phonocardiograph having a vibration sensor(detective sensor) like the above-mentioned heart sound microphone, an amplifier, a wave filter and an indicator, is produced in accordance with the Japanese Industrial Standard. The measurement of the phonocardiograph in accordance with the Japanese Industrial Standard is for detecting actuation abnormality of a valve and existence of an intracardiac shunt. However, in regard to very minute signal deriving from coronary artery stenosis during diastole and having wide frequency band between 200 to 1200 Hz, it is impossible to match the acoustic impedance between the heart sound microphone and the body surface if the weight of the microphone is not 5 g and less and ideally 1 g. Therefore, it is impossible for the phonocardiograph in accordance with the Japanese Industrial Standard to detect the very minute acoustic vibration signal between 200 to 1200 Hz.

As above-mentioned,

1, In the conventional practice, the very minute vibration signal of which frequency band between 200 to 1200 Hz is out of the Japanese Industrial Standard, and the above signal is out of the frequency of the measured object of the phonocardiograph.

2, As the vibration intensity of such very minute vibration signal is very weak, it needs to be amplified over 100 dB in order to make the above signal to be the measured object. In the case of using an acoustic vibration sensor like an microphone and an accelerometer as the detective sensor of the phonocardiograph for the above amplification, the matching of the acoustic impedance between the sensor and the body surface cannot be taken since the weight of the sensor becomes over 200 g.

3, Though the sensor technology by the displacement gage principle is in the conventional practice, the satisfied detection cannot be carried out because the sensitivity is insufficient and the vibration signal of the object is buried in the noise.

4, A time resolution is also insufficient in the conventional practice using the vibration sensor such as a microphone by vibrating plate resonance or an accelerometer by charge generation based on enclosure resonance.

5, Though the phonocardiograph using the laser interferometer had not been devised, the object of this is the heart sound. There is no system which can perceive and detect the very minute displacement vibration signal like coronary artery stenotic, diastolic and other murmur.

SUMMARY OF THE INVENTION

The present invention has been made in view of the afore-described points of problem. It is therefore, a primary object of this invention to provide a (acoustically non-invasive) diagnostic system and method for coronary artery disease and others, which can detect the vibration signal of murmur deriving from the shape abnormality like stenosis of the blood vessel such as coronary artery being heart nutrition blood vessel, that is to say, detect the vibration signal of the murmur deriving from the stenosis of the coronary artery in its early stages, for it is possible to diagnose abnormal condition, prevent and treat heart disease and others.

According to the present invention, in one aspect thereof, there is provided a (acoustically non-invasive) diagnostic system for coronary artery disease and others comprising a detector of vibration signal of subject using pulsed laser beam, which is placed apart from the subject, and a detector of vibration signal of environmental noise, and vibration signal detected by the detector of vibration signal of subject and the detector of vibration signal of environmental noise is filtered for canceling internal noise and external noise, and the filtered vibration signal is amplified and recorded. That is to say, it comprises a complex-multiple vibration sensor system with a detector of vibration signal of subject using pulsed laser beam and a detector of vibration signal of environmental noise, and processing part which cancel internal noise of measuring instrument and external noise, amplify only the very minute vibration signal deriving from stenosis of coronary artery on body surface, and record the vibration signal as data.

According to the present invention, in another aspect thereof, there is provided a diagnostic system for coronary artery disease and others, which is characterized in that said detector of vibration signal of subject has one or a plurality of laser source head and vibration detective sensor with laser displacement gage and three-axial accelerometer. In this invention, perception and detection of stenotic vibration signal on body surface is conducted in noncontacting technique, and pulsed laser beam is used in vibration detective sensor for input vibration signal, which is harmless to skin. The laser source head is fixed to a support or is slided along the support and is incorporated in the sensor system.

According to the present invention, in further aspect thereof, there is provided a diagnostic system for coronary artery disease and others, which is characterized in that said detector of vibration signal of environmental noise has three-axial accelerometer and supersensitive microphone. That is to say, the detector of vibration signal of environmental noise has the three-axial accelermeter which detects vibration signal of environmental noise deriving from laser source head and a bed and others, which is incorporated in the complex-multiple sensor system. The supersensitive microphone is used to detect external noise deriving from measuring environment, which is fixed like such laser source head and is incorporated in the complex-multiple sensor system.

The complex-multiple sensor system comprises hardware including the deal of the internal noise deriving from these measuring instruments, which is a low-noise measuring system utilizing the detectors compound by optimization according to software utilizing measuring equation.

According to the present invention, in still further aspect thereof, there is provided a diagnostic method for coronary artery disease and others comprises the steps of detecting vibration signal by a detector of vibration signal of subject using pulsed laser beam which is placed apart from the subject and a detector of vibration signal of environmental noise, filtering said vibration signal to cancel internal noise and external noise, amplifying the filtered vibration signal and recording said filtered vibration signal. That is to say, the diagnostic method for coronary artery disease and others perceives and detects the very minute vibration signal of the murmur deriving from stenosis of coronary artery on the body surface in noncontacting technique by using the above diagnostic system for coronary artery disease and others using pulsed laser beam being harmless to skin.

The foregoing objects, other objects as well as the specific construction and function of the present invention will become more apparent and understandable from the following detailed explanations thereof, when read in conjunction with the accompanying drawing.

BRIEF EXPLANATION OF THE ACCOMPANYING DRAWING

DESCRIPTION OF THE PREFERRED EMBODIMENT

Figure 1:
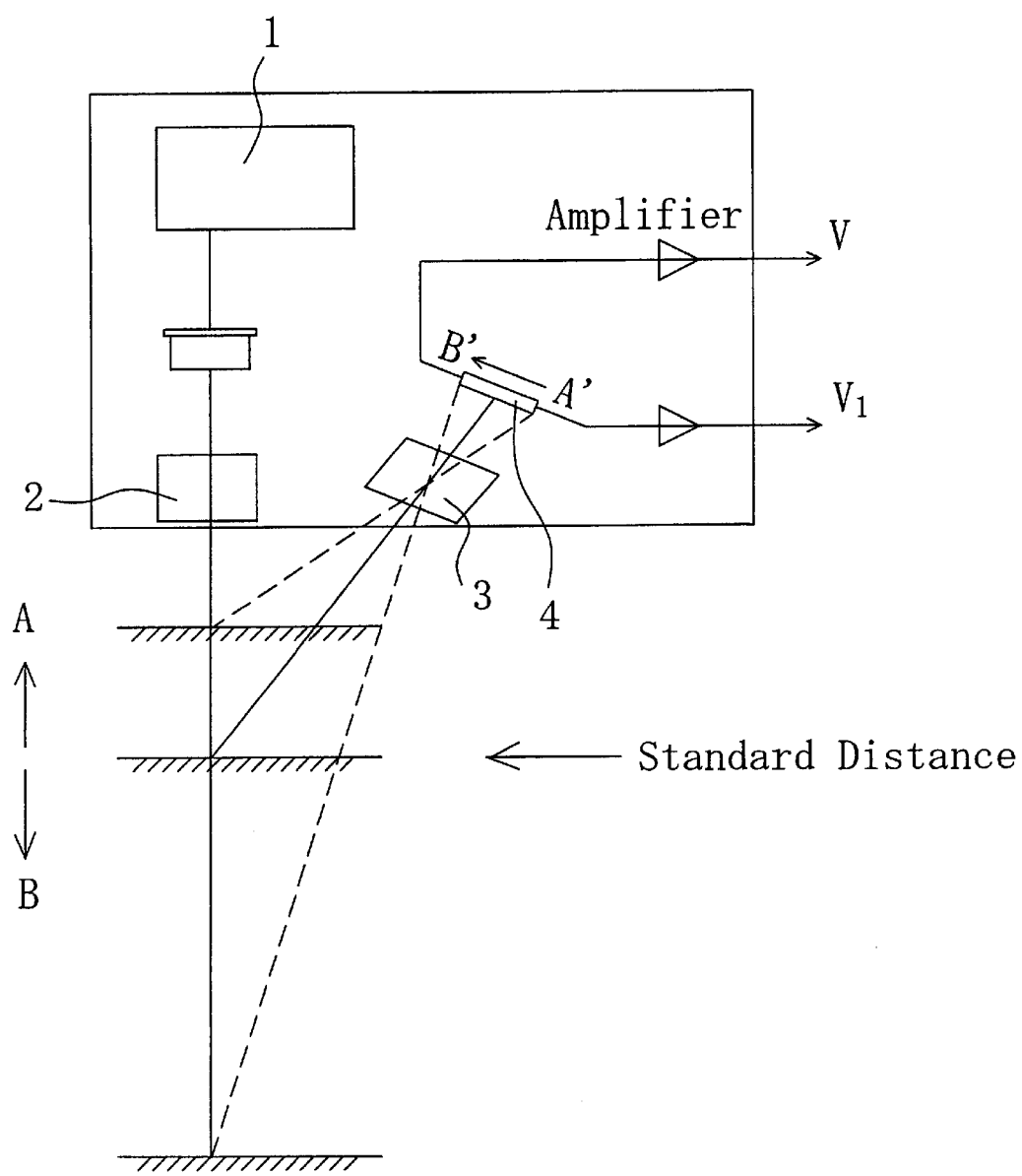
FIG. 1 is a diagram showing the measuring principle of displacement of vibration utilizing pulsed lazer beam.

The present invention with a complex-multiple sensor system has a vibration displacement gage utilizing the Doppler phenomenon and regular reflection and diffuse reflection of laser diode visible pulsed laser beam on body surface. Based on the data gathered by the basic research done until now, in order to set measuring range, working distance, resolution for entering the frequency and the amplitude of displacement element of the very minute stenotic murmur of coronary artery containing each displacement element of respiratory movement, heartbeat fluctuation component, heart sound fluctuation component and heart murmur fluctuation component in displacement of chest wall into dynamic range, the wavelength of pulsed laser beam is 760 nm, and the pulse duration is 10 um, and the sampling frequency is 50kHz, and the laser safety standard is class 2 ("class 2" in the following), for example.

A supersensitive and high-resolving three-axial accelerometer is attached to laser source head in order to detect vibration signal of internal noise and external noise deriving from environment of laser source head, which is included in a complex sensor. Since the measurement in bedside is interfered by noise, the accuracy of the measurement is reduced or the measurement itself cannot be carried out. Therefore, the supersensitive three-axial accelerometer as a vibration sensor is incorporated in the system, in order to monitor the vibration signal of internal noise and external noise deriving from environment of laser source head directly and visually as a noise signal to correct, and cancel the above vibration signal from the A vibration signal of the body surface as a vibration signal to measure by using time average, ensemble mean and differential composition of bridge circuit and others.

A detector of vibration signal of measured object with the united complex sensor is fixed to a support or is attached to a support which is allowed to slide along the support. The measuring equation is set in the complex-multiple sensor system or the diagnostic system in order to remove environmental noise, accordingly, the specific fixed apparatus or device which has been considered until now is not required. A supersensitive microphone is incorporated in the system in order to monitor environmental noise deriving from measuring environment. Therefore, the system can monitor the vibration signal of the environmental noise by visualizing it as a referred vibration signal of environmental noise, and cancel the vibration signal of the environmental noise from the vibration signal of the body surface as a vibration signal to measure.

High damping gradient filters (about 1000 dB/oct) are multiply put on a amplifier with low noise and high amplification factor. It may be made to be a system that a signal of measured displacement from the laser source is extracted as an acceleration signal by combining differentiating circuits, and it is displayed and recorded. As above-mentioned, the noise is removed on the hardware.

Each objective amplified signal is converted into frequency domain by a signal processing such as the linear prediction processing and is made to be a power spectrum. Thereafter, the noise signal is canceled from the objective measured signal and only the frequency of the objective signal is extracted, displayed and recorded.

The coronary artery blood flow causing the objective measured signal is one during the heartbeat diastole. The frequency band is designed to be the 100 Hz width, as it is a unsteady quantity with the fluctuation. The domain from II heart sound being stop consonant of arterial valve in the heart sound to the time after 100 milliseconds of the II heart sound in the maximum is recorded for 10 heartbeats. Therefore, the measuring time is about 10 seconds, and this time is very shorter than the measuring time of using electrocardiogram, 24 hour electrocardiogram, motion loaded electrocardiogram or scintigram in the conventional noninvasive inspection of coronary artery disease.

The low S/N ratio in the hardware in the measuring system is supplemented by the software, and noise element entered from a commercial power supply is removed by using a filter transformer. Therefore, the measuring system is the sensor fusion measuring system as a whole.

The theoretical background of acoustic diagnosis of coronary artery stenosis in the invention is described in the following.

1) Rheology of coronary artery and others

As blood shows a feature in which the viscosity increases with the shear rate increasing, it is handled as a non- Newtonian fluid of an incompressibility. In case of fluid with such viscosity flowing in a circular pipe of which diameter and flow rate completely change, the flow pattern of that is divided into two different flows, namely, laminar flow and turbulent flow. Critical Reynolds number (Re) generating the transition from laminar flow to turbulent flow is shown in the following.

Re<2,300 laminar flow
2,300<Re<2,500 transition flow area
Re>2,500 turbulent flow Re is shown as equation (1).

$$Re = \rho \cdot U \cdot r / \eta \tag{7}$$

ρ: blood density 1.0 (g/cm³),
U: blood flow velocity per unit time
r: blood vessel radius,
η: blood viscosity 0.04 (g/cm·s)

From that diameterthickness of right or left coronary artery in trunk is about 5~6 mm in the maximum, it is considered that the Reynolds number in the trunk of right or left coronary artery is about 200~300 in rest condition and it is about 1500 or less in intense motion, therefore turbulent flow is not generated in coronary artery through all cardiac cycle. However, in case that a local change of a diameter of the blood vessel is generated by deformation of the vessel wall or arteriosclerosis the flow may be locally disturbed even if the Reynold's number is smaller than 2300.

2) Local turbulence of blood flow "jet"

The factor causing local turbulence of blood flow is described in the following.

When blood vessel in heart ventricle wall is strongly pressed by contraction of cardiac muscle, coronary blood flow decreases. Therefore, the coronary blood flow mainly flows during cardiac muscle diastole, which is different from other artery. And left ventricle wall is thicker than right ventricle wall, therefore, left coronary artery blood flow is accelerated at diastole, and it reaches the largest blood flow from the almost zero. When stenosis occurs, the fluid is accelerated at diastole and it is immediately decelerated afterwards. On the assumption that it is possible to disregard a degree of effect of viscosity since it is minute, the Bernoulli's equation is shown as equation (2).

$$P + \rho g h + (\tfrac{1}{2})\rho U^2 = K (\text{constant}) \tag{2}$$

P: pressure,
ρ: fluid density,
U: flow velocity

In case that the equation (2) is applied for a cross section of a stenotic site and a cross section close to the cross section of the stenotic part which is located in the downstream of the stenotic part on the assumption that the tube is horizontal (h=0), the flow velocity of the position close to the stenotic part in the downstream is smaller than that of the position of the stenotic part, while the pressure is higher than that. Therefore, the reflux is generated along the tube wall in the downstream of the stenotic part, it meets with the flow of Z direction at the S point (the peeling point) of the position of the stenotic part and changes the direction. Thereafter, it joins the mainstream and flows to the downstream.

Thus, circulating flow is formed between the peeling point S and the reattachment point R. This condition is called "jet" and it is known that the flow of this condition is very unstable. In case of the two-dimensional jet, it has been clarified that threshold value of Reynold's number is Re=4.0, when turbulent flow is formed. That is to say, in case of the coronary artery of the stenotic condition, it is considered that the turbulent flow condition is generated on condition that the Reynold's number is lower than usual.

And, the vibration frequency of external wall by the generation of turbulent flow is obtained by Strouhal number S shown as equation (3).

$$S = (f \cdot d) / U \tag{3}$$

f: frequency of blood vessel vibration,
d: internal diameter of blood vessel

Furthermore, by using the equation of continuity, the frequency of blood vessel vibration which arises in the condition that the internal diameter of blood vessel becomes d [mm] when the stenosis of the coronary artery occurs is shown as equation (4).

$$f = (2/d^3) \times 10^3 \tag{4}$$

3) Transmission of the jet vibration to the chest wall

There are several cases in which stenotic murmur of coronary artery could be caught in a clinical demonstration in the past. The murmur cannot be caught generally as it is very minute and is attenuated in inverse proportion to an involution of a frequency from a source of vibration. It is considered as a cause that the murmur has been buried in other biological vibration with the attenuation. Vibration of coronary artery stenosis which is very minute intermingles with displacement vibration of chest wall. Therefore, it seems to be detectable in a body surface if filter processing, amplifier processing, signal processing are carried out by using the high-resoluble and supersensitive vibration sensor.

Subsequently, the measuring principle is discribed. Vibration signal being mechanical and physical signal arises in organism. In the vibration signal, there are I heart sound deriving from switching the heart valve (sound of which an atrioventricular valve between heart atrium and heart ventricle closes), II heart sound (sound of which an arterial valve between blood vessel and heart ventricle closes), extra heart sound, valve abnormal sound and murmur deriving from coronary artery disease. The vibration signal tarvels to the body surface vibrating biotissue. The mechanical vibration transmitted to the chest wall becomes displacement signal. In the body surface, heart sound and cardiac murmur such as that are caught by a stethoscope as vibration of the surface are caught and are recorded by a phonocardiograph, which is displacement signal.

The turbulent flow murmur vibration based on stenosis and diastole of coronary artery and others are buried in the noise because the the amplitude is very weak, in comparing with usual heart sound and murmur, and the frequency band of the vibration shifts in high frequency area. These are also the displacement signal on the chest wall. Generally, in the record using the phonocardiograph, the stenotic vibration is buried in the basic line and it cannot be detected and distinguished as a stenotic murmur because the vibration is very minute.

For detecting the very minute stenotic murmur vibration, in order to detect the very minute stenotic vibration transmitted is needed, which is difficult in the conventional phonocardiograph in view of objective vibration frequency band, amplification degree, S/N ratio and others. The essential problem is that the microphone which catches the vibration signal has an important defect. The defect is that the vibration transmitting characteristics of the chest structure lowers and changes by the weight of the microphone, namely a mismatching of an acoustic impedance is generated, because the microphone contacts the body surface(using the contacting technique of a vibration perception detector). It has been known in our precedent research that the resolution of the vibration detector is not sufficient even if such a supersensitive accelerometer is used.

Though the detector perceiving displacement of vibration (the contacting technique of a vibration perception detector) was produced, which is directly applied to the body surface as a displacement gage in order to take the matching of the impedance, it has also been known in our precedent research that the detective sensitivity is not sufficient and it is not used as a practical use.

Then, it seems that a noncontacting technique has to be chosen as a structure of the vibration perception detector. In order to detect the vibration of the body surface by the noncontacting technique, it is considered that an acoustic wave (an ultrasonic wave) or a beam of light is considered as the medium and the reflection is utilized. However, in order to detect the very minute displacement amplitude accurately, laser beam of which monochromaticity, directionality and convergence are excellent is only allowed to be chosen at the present time. The transmissivity of that is low, the reflectivity is high and the light source focus can be as small as possible.

The displacement signal measured by the laser displacement gage is integrated by the chest tissue while the acceleration signal by stenosis and diastole are transmitting to the chest wall. The detected displacement signal on the chest wall can be distinguished by the frequency domain since the frequency of the displacement signal of the vibration does not change and only the phase of that changes. Thus, coronary artery disease can be diagnosed through distinguishing the displacement signal containing the turbulent flow vibration deriving from the coronary artery stenosis by the frequency domain. The amplitude strength can be distinguished as a power.

The measuring principle of displacement of vibration utilizing pulsed lazer beam is shown in FIG. 1. In FIG. 1, 1 is a laser diode driving circuit, 2 is a projection lens of the laser beam, 3 is a reception lens and 4 is a light position detecting element.

A laser diode in Class 2 is used as a laser beam being harmless to organism, and the near infrared area of 670 nm wavelength of that is utilized, and the displasement is output as a displacement magnitude signal(it is exemplified as A←→B and A'←→B' in FIG. 1), which is based on the principle of triangulation. The minute vibration of the light source is generated in the environment even if the laser beam is used as signal detecting medium, which becomes internal noise deriving from the measuring system. Therefore, the measurement with monitoring is carried out to also cancel this internal noise. And, as the minute vibration of the body of the subject also becomes a kind of internal noise deriving from the measuring system, the measurement with monitoring is carried out in order to also cancel this internal noise.

A displacement of the body surface by respiration and a displacement of the body surface by heartbeat and others get mixed in the detected displacement magnitude signal as the internal noise of measured object. In order to narrow down the signal frequency which is necessary for the distinction of the signal of the vibration deriving from the coronary artery disease, the displacement signal is passed through a lowpass filter and a highpass filter which have sufficient attenuating gradient.

As described above, the acceleration signal deriving from coronary artery stenosis during diastole becomes the displacement signal by passing through the tissue. Therefore, it is necessary to differentiate the displacement signal of the body surface which is detected by using the laser beam as a signal detecting medium on the principle of triangulation, in order to convert it into the acceleration signal. And the displacement signal can be distinguished by the frequency domain as the frequency of that does not change by the differential and integral operation.

The signal of the measured object can be taken out from the time domain at need. As the signal of the measured object deriving from coronary artery disease is based on a beating period of heart, an electrocardiogram is used as a scale of the time domain. In the electrical processing of the measuring signal, in order to reduce systematic errors, the power supply which sufficiently consider the internal noise deriving from the measuring apparatus and the entering noise to the measuring system and the ultra-low noise and supersensitive amplifiers and others are used, and the connection method and others are done.

The stenotic murmur signal in the measured signal of the outputting object is formed as a whole, which contains the remained noise signal deriving from the measuring system which cannot be removed and the noise signal deriving from the measured object. In order to acquire the signal of the measured object which is buried in the noise by exceeding the S/N ratio of the system, it is separated from the other noise by using the technique of the signal processing. The technique of the signal processing follows our precedent research.

It has known in our precedent research that the frequency of the noise vibration of the stenotic murmur and the power value of that are determined by the internal diameter of the stenotic site, the flow velocity, the viscosity of the blood and others. Therefore, the signal of the object is compared by converting into the frequency domain. Then, it is displayed as the power value of the generating frequency after converting into the frequency domain by using the maximum entropy method (MEM) as means of the linear prediction.

Figure 2:
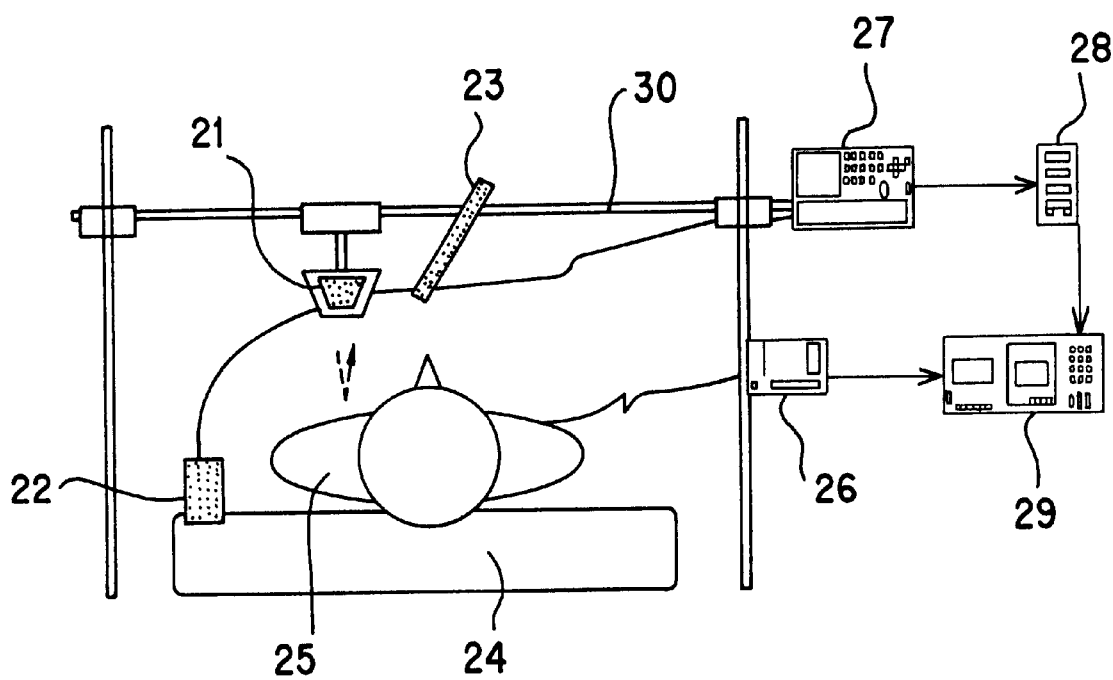
FIG. 2 is a diagram showing the embodiment of the diagnostic system for coronary artery disease and others in the present invention.

In the embodiment, it is measured by using a complex-multiple sensor system shown in FIG. 2 as a basic measuring system. In FIG. 2, 21 is a detector of vibration signal of measured object, which has one or a plurality laser source head and a vibration detective sensor of measured object (complex sensor) with a laser displacement gage and a three-axial accelerometer, 22 is a vibration detective sensor of environmental noise for a bed using a three-axial accelerometer in a detector of vibration signal of environmental noise, which is incorporated with the detector of vibration signal of measured object into the system. 23 is a supersensitive condenser microphone for detecting external noise of measuring environment, which is included with the above 22 in the detector of vibration signal of environmental noise, and which is fixed in the same way as the laser source head and is incorporated with the detector of vibration signal of measured object into the system. And, in FIG. 2, 24 is a consultation bed, 25 is a subject, 26 is an electrocardiograph, 27 is a filter having a high-pass filter and a low-pass filter, 28 is an amplifier and 29 is a DAT recorder. The united detector of vibration signal of measured object 21 is placed apart from the subject 25, which may be fixed to a fixed support 30 or be made to slide along the fixed support 30. The murmurs, internal and external noises are detect by the detector of vibration signal of measured object and the detector of vibration signal of environmental noise, and the vibration signal containing the murmur, internal and external noises are send to the filter 27, and the filtered vibration signal is amplified by the amplifier 28 and is recorded on the DAT recorder 30.

(1) Acquiring the vibration signal of the measured object

It is possible to measure in a lying position or in a sitting position and others because the measurement is done in a noncontacting technique. It is measured by fixing a projecting laser beam to the left sternal border of a left fourth intercostal space which corresponds to the front of a heart, or by sliding a plurality of laser source heads or one laser source head over the left back on the position without lung between the heart and the chest wall, which is done for about 10 seconds stopping respiration. The reason for measuring without respiration is to avoid effect of vesicular sound by the respiration anatomically. In the precedent research, it has been known that the frequency band of the stenotic vibration deriving from the coronary artery stenosis almost ranges from 200 Hz to 1000 Hz. The signal is filtered by the high-pass filter at 200 Hz and is filtered by the low-pass filter at 1000 Hz, and it is possible to set from 100 Hz to 1000 Hz. According to the superscription, it is possible to acquire the above frequency band with excellent S/N ratio. The gain of the amplifier 28 is approximately set from 200 times to 1000 times. The measurement is done for 10 heartbeats of a subject, namely for about 10 seconds. This measured signal is recorded with the electrocardiogram signal in the DAT 29.

The acquired signal is converted from analog to digital at 2 kHz as a sampling frequency, and is incorporated into the computer. The maximum entropy method (MEM) is used for analyzing in the frequency domain. The objective position of the frequency (spectrum) analysis is set at auxocardia from the R—R interval on the electrocardiogram. Though the spectral power by the MEM is shown as a relative value, it needs to be compared not by a relative value but by a absolute value. Then, the power spectral density is integrated on each 100 Hz frequency band. The reason for the 100 Hz interval is that it seems that coronary artery blood flow in diastole of heart is changeable and unsteady.

Figure 3:
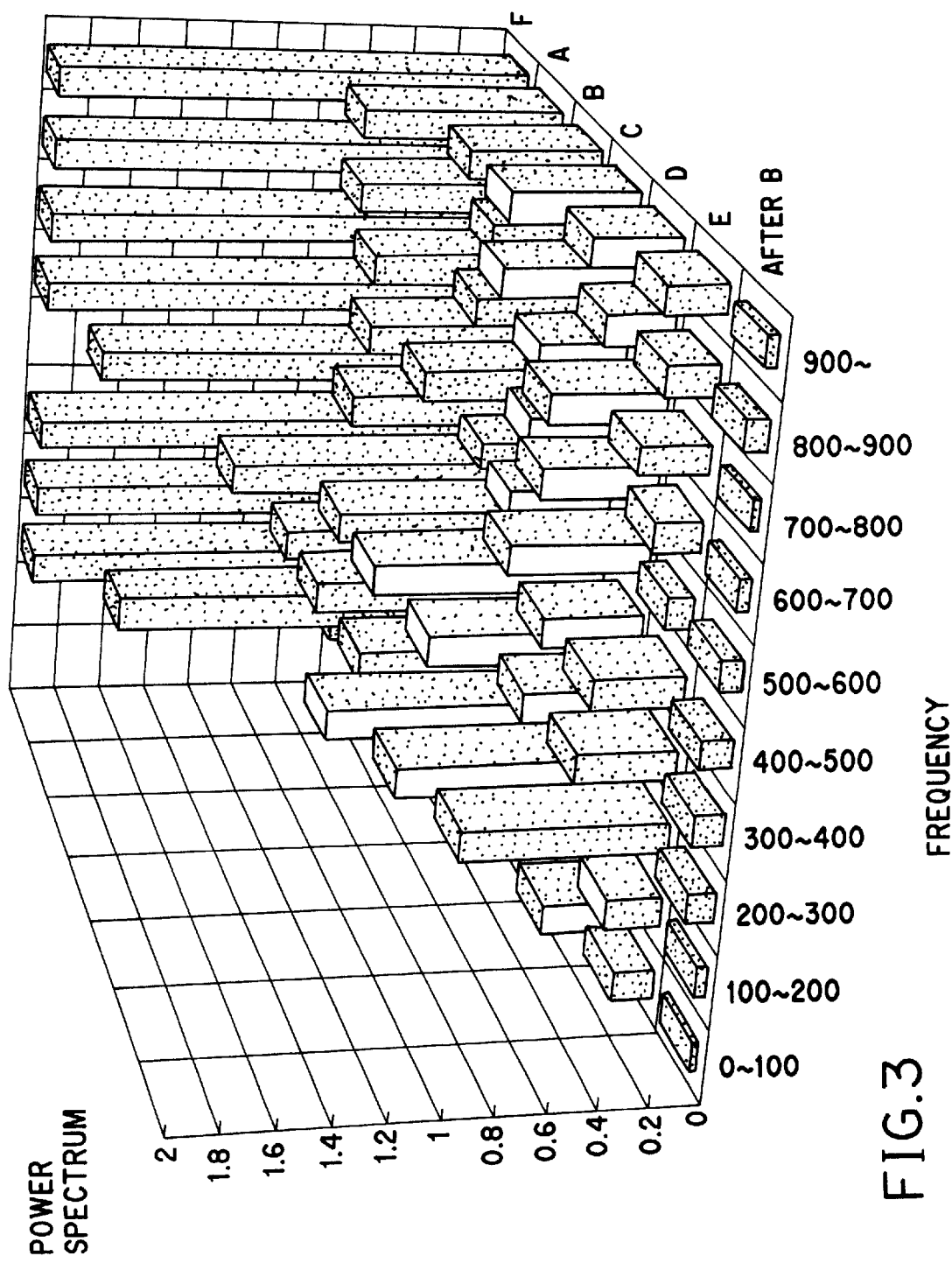
FIG. 3 is a histogram showing several instances of mean value of power spectrum strength of 10 heartbeats.

The histogram showing several instances of the mean value of the power spectrum strength of 10 heartbeats is shown in FIG. 3. F, A, B and others in FIG. 3 are the testee, and After B is a testee after a coronary artery bypass operation. The axis of abscissas shows frequency and the axis of ordinates shows power spectrum in FIG. 3. The rows of the amplitude strength correspond to the number of stenotic sites. By comparing the histogram with the findings of the coronary angiography which is done independently, it is known that a vibration with a strong power spectrum is the vibration of the stenotic murmur.

Figure 4:
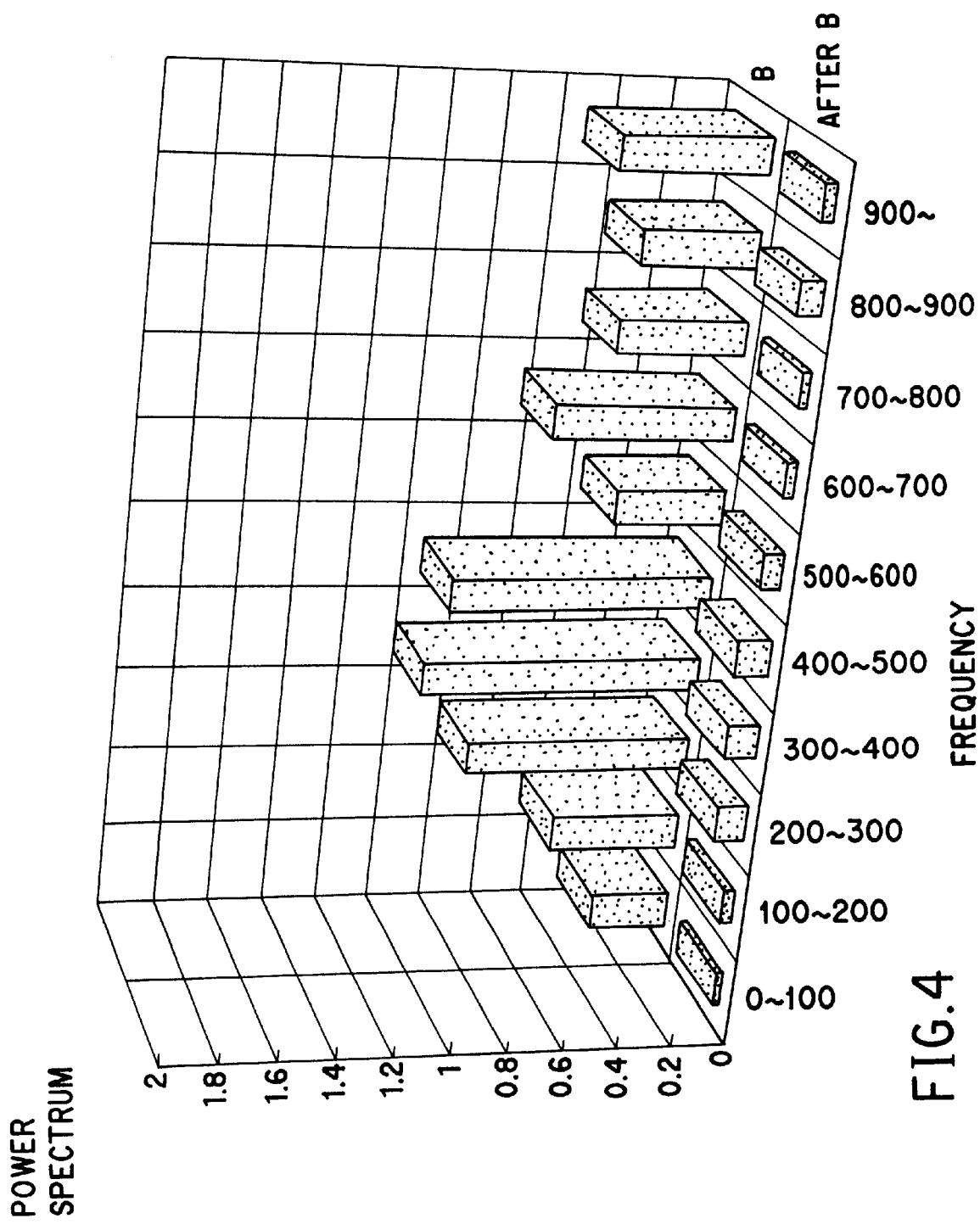
FIG. 4 is a histogram showing a preoperative and postoperative instance of mean value of power spectrum strength of 10 heartbeats of a coronary artery bypassed patient.

And the histogram showing a preoperative and postoperative instance of the mean value of the power spectrum strength of 10 heartbeats of a coronary artery bypass operative patient is shown in FIG. 4. B shows the preoperative and After B shows the postoperative in FIG. 4.

Figure 5:
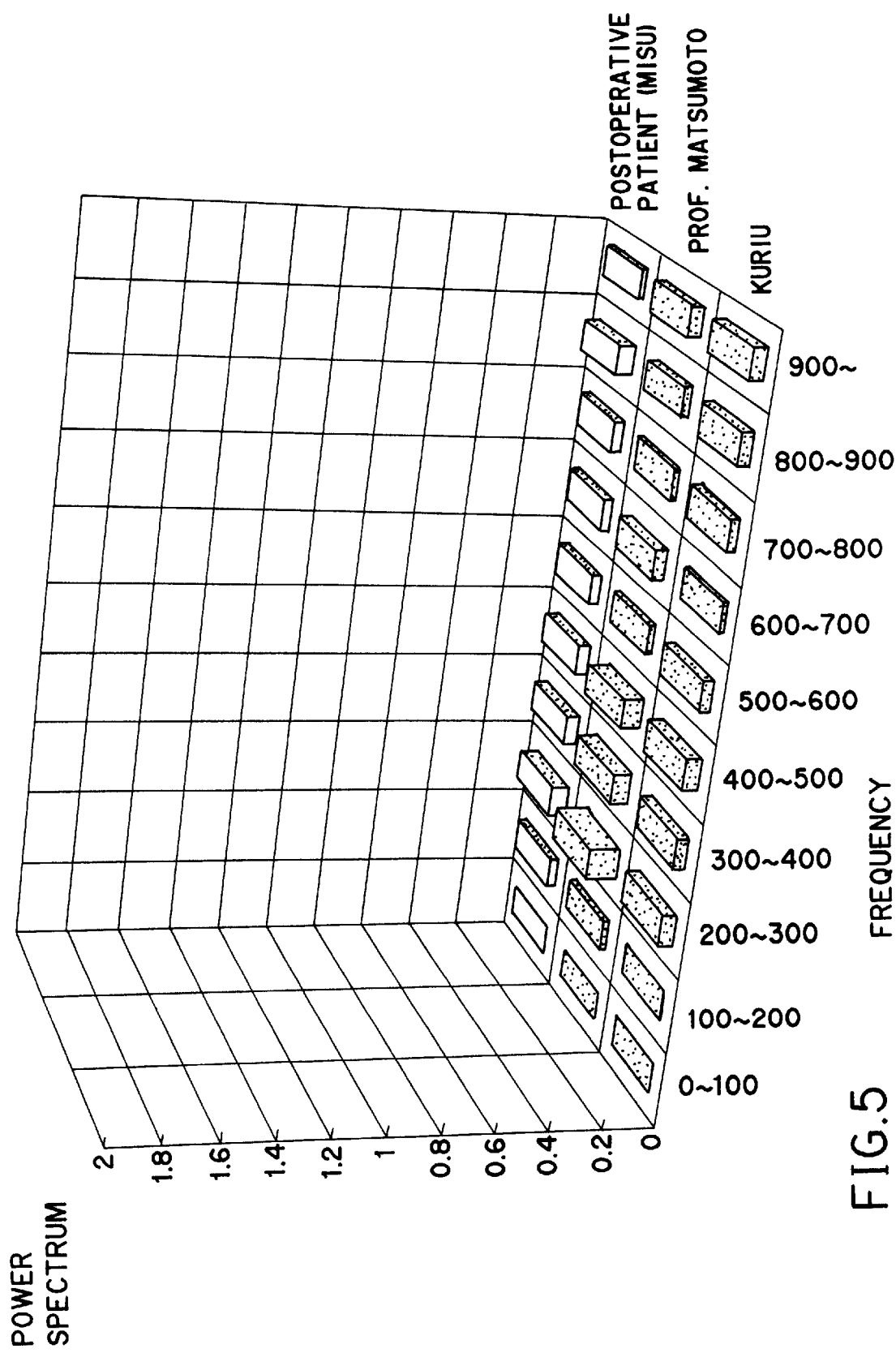
FIG. 5 is a histogram showing a measured instance of two healthy persons and a person whose blood flow improvement has been confirmed by coronary angiography (CAG) after a bypass operation.

FIG. 5 shows the findings of two healthy persons who seems to be nomal though the coronary angiography is not carried out and of a person whose blood flow improvement has been confirmed by the coronary angiography after a bypass operation. It is obvious that the amplitude level of the healthy persons is very lower than that of the coronary artery stenosed person in FIG. 4. The amplitude level of the postoperative patient is the same as that of the nomal persons, since the blood flow of the coronary artery is improved. And, it is known that the noise of the stenotic place by the superfluous vibration disappears, since the stenosis is canceled by forming the bypass and the blood flow increases.

[Effect of the invention] Since the (acoustically non-invasive) diagnostic system for coronary artery disease and others with a complex-multiple sensor system and the diagnostic method for coronary artery desease and others using the above diagnostic system in the present invention, are of such constitution as have been described in the foregoing, they have the following effect.

1, By using the present invention, it is possible that the vibration signal of murmur is detected, which derives from shape abnormality like stenosis of the blood vessel such as the coronary artery being heart nutrition blood vessel. Then, the vibration signal of the murmur deriving from the stenosis of the coronary artery can be detected in its early stage, and diseased condition can be diagnosed, and heart disease can be prevented or treated.

2, In addition, it is also possible to detect the muscle sound in systole and diastole of myocardium and diagnose a heart failure or a dysfunction of motion muscle and others. Since it contains the function as a phonocardiograph and its time resolution and its frequency resolution are very high, it is possible to detect information that the conventional phonocardiograph cannot measure.

3, Since the displacement vibrograph of noncontacting technique acquiring the vibration displacement magnitude by comparing the amount of incident light to the amount of reflected light is applied to the sensor detecting the acoustic vibration, it is possible to remove the problem of unconsistency of the acoustic impedance between the vibration detective sensor and the body surface, and measure the vibration displacement magnitude in the condition that it is transmitted to the chest wall.

4, The laser beam of which monochromaticity, convergence and directionality are excellent is used as a medium of measuring the displacement magnitude. The laser beam is selected from laser diode, and the character of its wavelength and strength of the laser beam is that its permeability is low and that is harmless to the organism.

5, The measured displacement magnitude may convert into the the acceleration quantity by the differential processing. In the present invention, the three-axial accelerometer is used for monitoring and canceling the vibration deriving from the environment such as laser source, and the microphone for detecting reference noise is used for monitoring and canceling the influence of the environmental noise vibration signal on the measured object signal, and the noise signal is converted into the frequency domain. Consequently, the systematic error is reduced and the S/N ratio of the measured object signal is improved.

6, Moreover, the measured signal is divided from the internal and the external noises deriving from the environment by comparing the frequency domain in the signal processing, and the noises can be removed.

Although the present invention has been described in detail in the foregoing with reference to the preferred embodiment thereof as shown in the drawing, the invention is not limited to the embodiment alone, but those persons skilled in the art may be able to make various improvements in, and modifications to, the embodiment without departing from the spirit and scope of the invention as recited in the appended claims. Especially, the above diagnostic system is allowed to use in order to diagnosing for other disease by detecting murmur deriving from superficial blood vessel such as femoral artery and carotid artery, and others.

What is claimed is:

1. A diagnostic system for coronary artery disease and others comprising:

a detector of vibration signal of subject using pulsed laser beam, which is placed apart from the subject, and measures vibration signal of subject in an area of the heart of the subject;

a detector of vibration signal of environmental noise;

wherein vibration signal detected by said detector of vibration signal of subject and said detector of vibration signal of environmental noise is filtered for canceling internal noise and external noise, for detecting a vibration deriving from the coronary artery disease in a frequency band between 200 Hz and 1000 Hz, and the filtered vibration signal is amplified and recorded.

2. A diagnostic system as defined in claim 1, which further comprises said detector of vibration signal of subject having one or a plurality of laser source heads and vibration detective sensor with laser displacement gage and three-axial accelerometer.

3. A diagnostic system as defined in claim 1, which further comprises said detector of vibration signal of environmental noise having three-axial accelerometer and supersensitive microphone.

4. A diagnostic system as defined in claim 1, wherein internal noise is canceled by filtering out frequencies other than frequencies in the frequency band.

5. A diagnostic system as defined in claim 4, wherein frequencies other than the frequencies in the frequency band are filtered out by filtering out frequencies lower and higher than the frequency band.

6. A diagnostic system as defined in claim 5, wherein said detector of vibration signal of subject has a vibration displacement gage utilizing the Doppler phenomenon.

7. A diagnostic method for coronary artery disease comprising the steps of:

detecting vibration signal by a detector of vibration signal of subject using pulsed laser beam which is placed apart from the subject and measures vibration signal of subject in an area of the heart of the subject, and a detector of vibration signal of environmental noise;

filtering said vibration signal to cancel internal noise and external noise, for detecting a vibration deriving from the coronary artery disease in a frequency band between 200 Hz and 1000 Hz;

amplifying the filtered vibration signal; and recording said filtered vibration signal.

8. A diagnostic method as defined in claim 7, wherein internal noise is canceled by filtering out frequencies other than frequencies in the frequency band.

9. A diagnostic method as defined in claim 8, wherein frequencies other than the frequencies in the frequency band are filtered out by filtering out frequencies lower and higher than the frequency band.

* * * * *